United States Patent
Penn et al.

(10) Patent No.: US 8,194,951 B2
(45) Date of Patent: Jun. 5, 2012

(54) METHOD AND SYSTEM FOR GENERATING DISPLAY DATA

(75) Inventors: Alan Penn, Rockville, MD (US); Scott F. Thompson, Vienna, VA (US)

(73) Assignee: Philips Electronics North, Cleveland, OH (US)

(*) Notice: Subject to any disclaimer, the term of this patent is extended or adjusted under 35 U.S.C. 154(b) by 772 days.

(21) Appl. No.: 12/088,301

(22) PCT Filed: Oct. 2, 2006

(86) PCT No.: PCT/US2006/038309
§ 371 (c)(1),
(2), (4) Date: Sep. 8, 2008

(87) PCT Pub. No.: WO2007/041429
PCT Pub. Date: Apr. 12, 2007

(65) Prior Publication Data
US 2009/0016582 A1    Jan. 15, 2009

(51) Int. Cl.
*G06K 9/00* (2006.01)
*A61B 5/00* (2006.01)
(52) U.S. Cl. ......... 382/128; 382/130; 382/224; 600/407
(58) Field of Classification Search .......... 382/128–133; 600/407–464
See application file for complete search history.

(56) References Cited

U.S. PATENT DOCUMENTS

| | | | |
|---|---|---|---|
| 4,907,156 A | 3/1990 | Doi et al. | |
| 5,133,020 A | 7/1992 | Giger et al. | |
| 5,881,124 A | 3/1999 | Giger et al. | |
| 6,309,353 B1 | 10/2001 | Cheng et al. | |
| 6,671,540 B1 | 12/2003 | Hochman | |
| 7,024,028 B1 * | 4/2006 | Bar Shalev | 382/131 |
| 7,088,850 B2 * | 8/2006 | Wei et al. | 382/128 |
| 7,400,755 B2 * | 7/2008 | West et al. | 382/128 |
| 2004/0258285 A1 * | 12/2004 | Hansen et al. | 382/128 |
| 2006/0247525 A1 * | 11/2006 | Huo et al. | 600/437 |
| 2009/0060297 A1 * | 3/2009 | Penn et al. | 382/128 |

* cited by examiner

*Primary Examiner* — Melissa Koval
*Assistant Examiner* — Emily Chan
(74) *Attorney, Agent, or Firm* — Browdy and Neimark, PLLC

(57) ABSTRACT

A method of aiding in the evaluation of lesions in a body using a plurality of sets of image data of sections of the body region in mutually parallel planes. Processing of the data requires several steps, including pixel intensity pattern recognition, ~ contouring of the regions of probable pathology, thresholding and 3-dimensional clustering, providing each pixel with a color representative of a selected opacity level and displaying an image of the region of interest where areas of probable pathological conditions are highlighted.

3 Claims, 6 Drawing Sheets

METHOD AND SYSTEM FOR GENERATING DISPLAY DATA

This work was supported in part by at least one grant R44CA85101 issued by the National Cancer Institute (NCI). The government may have certain rights in this invention.

TECHNICAL FIELD

The present invention relates to the detection and diagnosis of lesions. The invention relates more particularly to the generation of display data for aiding the diagnosis and detection of lesions in a body part. The starting point of the invention is technology disclosed in Provisional Application 60/647,756, filed on Jan. 31, 2005, and in international PCT application PCT/US05/15326, filed on May 3, 2005. The entirety of the disclosures of these applications are incorporated herein by reference.

BACKGROUND ART

In many prior systems for aiding such diagnoses, data are represented in three dimensions where two of the dimensions (x,y) represent spatial location on a grid of fixed size and the third dimension (w) is a representation of original source data. As an example, in magnetic resonance imaging (MRI) systems, the w dimension is image intensity, which represents signal strength from the imaging system. In the MRI example, the source signal is transformed to an image intensity signal to show a medically appropriate representation of the MRI image data in a way that satisfies limitations in intensity values imposed by the display system, e.g. $2^8=256$ discrete intensity levels. Linear transformations on the w-axis, such as windowing and leveling, are typically used to show the medically relevant portions of the image in the central portion of the displayed intensity scale. In many of these applications, the end-user could benefit from being able to distinguish and discriminate objects (e.g., lesions) within the source data on the basis of the original signal strength. However, the transformations from source signal to image intensity signal, which may vary from case to case, make this comparative analysis difficult and subject to error. In other systems, data are represented in 4 dimensions, where 3 of the dimensions represent spatial location (x, y, z) and the fourth dimension (w) is a representation of the source data. All discussions and descriptions for the invention in 2 spatial dimensions are readily extended to 3 spatial dimensions. While the term pixel is frequently used to refer to 2-dimensions and the term voxel is frequently used to refer to 3-dimensions, in this application we use pixel to refer to 2-dimensions and 3-dimensions.

Data obtained in this manner for one planar region will be referred to herein as a first data set.

In the example of medical MRI, the source signals from gadolinium-enhanced images of malignant lesions are frequently stronger than the source signals from gadolinium enhanced images of benign lesions. However, after the source data have been transformed to image intensities that have been adjusted to optimize medical diagnosis, where this optimization differs from case to case, it is difficult for the radiologist to evaluate the strength of the original magnetic resonance signal on the basis of the images that are presented.

The above-cited applications disclose a system, method and computer program product in which such first data sets are subject to computer processing to allow more accurate diagnosis of whether a lesion in an image is cancerous, benign, or of an uncertain nature based on the intensities of the pixels in the image.

The procedures disclosed in the above-cited applications were in terms of their application in medical-radiology for discriminating benign from malignant lesions on gadolinium-enhanced magnetic resonance images (MRI) on the basis of image intensity values where the image data being analyzed has 256 discrete intensity values and has been subjected to prior windowing and leveling operations according to known techniques to produce the first data sets. The procedures disclosed in the above-cited applications were first described in terms of images corresponding to a 2-dimensional spatial slice. The extension of those procedures to a set of 2-dimensional slices that comprise a 3-dimensional data set is described later therein. It is assumed that windowing and leveling is "reasonably consistent" between cases that are to be discriminated, conforming to standard medical practice, and for each case, a "landmark" showing the approximate location of the lesion, is known. The invention disclosed in the above-cited applications may be applied to any imaging system in which the goal is to evaluate the image intensity and spatial relationships of the pixels in the image, within the skill of the ordinary artisan.

Starting with the first data sets, and using standard thresholding and clustering algorithms, a cluster is grown around the landmark for each possible intensity value, which, according to one embodiment, starts with the highest (e.g., 255) and ending with the lowest (0). The clusters around the landmark form a nested, monotonically increasing (but not necessarily strictly increasing) sequence. At each possible intensity level, a region-of-interest (ROI) is constructed around the cluster in a particular shape such that the ROI is the minimal shape containing the cluster. According to one embodiment, the ROI is a minimal rectangular box, or rectangular hull, formed around the cluster. Other shapes may be used within the skill of the ordinary artisan. The ROIs also form a nested, monotonically increasing (but not necessarily strictly increasing) sequence. According to one embodiment of the present invention, where the ROI is a rectangular box, for each ROI in the sequence, the area of the ROI is computed by multiplying width by height. If the shape for the ROI is not a rectangular box, the area is computed using a different formula, depending on the ROI shape. If the characterization of the ROI being used is not the area, then a different formula may be used. As an example of a possible characterization other than area, in ultrasound, the ratio of width to height is important and this ratio can be used as the chosen characteristic. Further, if the ROI is depicted in 3-dimensions, instead of 2-dimensions, the volume of the ROI may be used instead of area.

A plot of ROI area vs. intensity level is a step function—the plot of ROI area vs. intensity may remain constant for several intensity levels and then "step" up to a larger size. The number of steps has been found to be highly predictive of whether the lesion is benign or malignant using images from a variety of MRI imaging systems and protocols. Moreover, the number of steps has been found to show a high degree of independence from other discriminatory features and to be useful as a component of a computer-aided-diagnosis or computer-aided-detection system. In the specific example shown here, an image of a lesion is interpreted as being benign if the number of steps is less than or equal to 9 and is interpreted as being cancer if the number of steps is greater than 9. These thresholds may be adjusted as appropriate by an ordinarily skilled artisan. Additionally, other numbers related to the characterization of the ROI may be used.

While the number of distinct ROIs is a function of shape and gradient of a lesion, it is relatively insensitive to transformations of intensity values, such as windowing and leveling, provided that these transformations are not extreme (e.g., the leveling cannot have reduced the image to a few intensities).

One embodiment of the invention disclosed in the above-cited applications can be alternatively described in a more general mathematical context as follows: A cluster is a set of connected pixels. A contour at level L is constructed by first generating a binary threshold image where a pixel in the threshold image has value 1 if the corresponding pixel in the grey-scale image has value $\geq L$ and has value 0 otherwise. A contour at level L is the set of pixels at the boundary of 0's and 1's on the binary image. The Outer Contour at level L is the contour at level L that encloses the landmark and is furthest from the landmark. The ROI at level L is a geometric object having a specified shape, such as a square or rectangular box, that is of minimal size around a cluster or contour.

1. Determine location of pixels in lesion. A "pixel" is understood to be the picture element at a specific location in the coordinate system of the image.

2. A landmark within the lesion is selected, either manually or automatically within the lesion. Clusters around the landmark are determined for each level L in a subset of possible intensity levels as determined by a predefined set of rules, and Outer Contours are determined for the cluster at each of the L's. For example, each intensity level within the image may be used, or some subset thereof, e.g., every other or every third intensity level may be sampled and used. In a more general context, other sets of closed paths around the landmark could be defined using other methods that are known, within the skill of the ordinary artisan.

3, Define a function, F, from the space of Outer Contours to the space of real numbers. In the specific method described above, for each L the Outer Contour is determined and the function is defined to be the area of the rectangle, F(C)=Area (B), where B is the ROI defined to be the minimal rectangle around the Outer Contour. In a more general context, the ROI B could be another polygonal shape around the cluster that forms a nested sequence over the range of intensity levels, and F could be any function that discriminates distinct elements defining characteristics of the ROI in the nested sequence, within the skill of the ordinary artisan.

4. Define a function, G, on the range of F over the set of Outer Contours $\{C\}$. In the specific method described above, $G(\{RangeF_C\})=M$, where M is the number of distinct elements in the Range (i.e., the number of times F, the area, changes values). In a more general context, G could be another function used to characterize the function F of step 3, within the skill of the ordinary artisan. Further, it is possible to only consider steps in the Outer Contours in a portion of the range, to consider the density of steps, or other appropriate functions, as will be readily understood by those of ordinary skill in the art.

5. Define a feature, i.e., whether the lesion is more likely cancerous, benign, or uncertain, based on the function G. In the specific method described above a single threshold is set at 9 to discriminate benign from malignant lesions. In the more general context, a different threshold could be used or multiple thresholds or another distinguishing characteristic of G could be used to indicate different likelihoods of being benign or malignant, within the skill of the ordinary artisan.

According to one embodiment, the invention as disclosed in the above-cited applications is implemented on a computer connected to an imaging device or Picture Archiving system, such as a MRI device or other suitable imaging device or hospital PAC system (see FIG. 1). For purposes of this disclosure, reference to a computer will be understood to mean interchangeably a computer that is separate from the imaging device, or one that is integrated in the imaging device, wherein communication between the user and the computer (i.e., input device and display) is through the imaging device console, such as an MRI console. According to this embodiment, the computer has an input device (e.g., keyboard and mouse), a display device (e.g., monitor), and a processor. The processor can be a known system, having a storage device, a central processing unit (CPU), and other known components (not shown). The computer can be implemented separately, or as part of the imaging or archiving device. In the latter case, the display and input device of the imaging or archiving device could be used to interface with the computer, rather than separate components.

Source data consists of pixel intensities of an image derived from the MRI signal captured after use of contrast agent (POST) and pixel intensities of an image derived from the MRI signal captured before use of contrast agent (PRE). Pixel intensities of a subtraction (SUB) image are obtained by subtracting the pixel intensities of PRE from pixel intensities of the POST (FIG. 2, step 1). If there are multiple post contrast images, a set of post contrast images is selected according to predetermined criteria. For example, post contrast images that correspond to peak enhancements may be used. Indication is given below whether SUB or POST is used for each step in the procedure.

According to one embodiment of the invention disclosed in the above-cited applications, parameters are set to: Q=25 mm$^2$, N=4, (FIG. 2, step 2), where Q is a lower bound on the area of the lesion, and N is determined heuristically to approximate the point at which the cluster effectively grows into background noise. The meaning of the number N is explained as follows: A minimum size of the lesion, E, is obtained by first constructing the Outer Contours at each intensity level, L, starting with the intensity level of the landmark and decrementing, until a level is reached for which the area within the Outer Contour first exceeds Q, the lower bound set by parameter. As intensity level L is further decremented, the area within the Outer Contour increases, ultimately encompassing the entire image, including background tissue outside of the lesion. For each of these Outer Contours, the mean gradient along the corresponding path on the Post image is computed. The level IMax, which corresponds to the maximum mean gradient, is selected and the area within Outer Contour of level IMax is the minimum area of the lesion. As the index L is decremented beyond IMax, the area within the Outer Contours increases. When the area first exceeds N times the minimum area of the lesion, the Outer Contour is assumed to have extended beyond the lesion and grown into the background tissue.

The "step feature" is a measurement of a grouping of enhancing pixels on the SUB image, as determined by a landmark, L, defined to be a single pixel in an enhancing group. (FIG. 2, step 3). In general, different landmarks within the same enhancing group will produce different step feature values. The landmark that is used can either be determined by an expert using image and contextual information or determined automatically from image processing and/or histogram analysis. In the implementation according to one embodiment, histogram analysis is used to identify pixels intensities that are likely to be part of a lesion, and cluster analysis is used to identify collections of enhancing pixels that are likely to comprise the lesion. The centroid or other identified region of the cluster of enhancing pixels can be used to identify the landmark. In the implementation according to another embodiment, a radiologist draws a rectangular, or other shaped, ROI around the lesion and the landmark is the center point of the ROI. This ROI is input to the processor by the input device.

The step feature will now be described algorithmically, and it is assumed for this discussion that there are 256 possible pixel intensity levels on the images, ranging from 255 (highest) to 0 (lowest). Let I(L) denote the pixel intensity at the landmark, each pixel having a particular intensity I in the range of $0 \leq I < 255$. According to another embodiment of the invention, each pixel may have a particular intensity I in the range of $0 \leq I < 2^N$, where N is an integer >1, which would include image displays with 128, 512 or 1024 intensity levels. Starting with level I=I(L) and decrementing I at each step, we construct the cluster of pixels that are 4-connected to L and have intensity level $\geq I$. A cluster is 4-connected if there is a 4-neighbor path from every pixel in the cluster to every other pixel in the cluster where pixels are 4-neighbor if they are side-by-side or one directly above the other. Other forms of connectivity, including, but not limited to, 8-neighbor in 2-dim and 6-neighbor, 18-neighbor or 26-neighbor in 3-dim can also be used. (See *Digital Image Processing*, Gonzalez and Waitz, $2^{nd}$ Edition, Adison & Wesley, 1987.) These clusters form a monotonically increasing set $\{C_N, C_{N-1}, \ldots\}$, with Function$(C_N) \leq$ Function$(C_{N-1}) \leq \ldots$ as the index is decremented. When in 2-dimensions, the Function is the Area of the cluster. When in 3-dimensions, the Function may be the Volume of the cluster. Other alternatives also can be used, within the skill of the ordinary artisan. This process is continued until intensity level equals II, where Function$(C_{II}) \geq Q$, where the Function is Area when in 2-dim, and Volume when in 3-dim. II is the first level at which the Function of the Outer Contour exceeds the lower bound of the lesion as set by the parameter. (FIG. 2, steps 4-9). Step 5 computes the binary threshold image used to derive the Outer Contour and Step 6 computes the Function (such as area or volume) within the Outer Contour.

An $I_{max}$ and an $I_{min}$ value can be determined using a histogram analysis. Alternatively, according to one embodiment, starting with intensity level J=II and decrementing by J at each step, the mean gradient on the border of the 4-connected set $C_J$ (MeanGrad(J)) is computed using data from POST. (FIG. 2, step 10). The intensity level at which MeanGrad is maximum defines level $I_{max}$ (FIG. 2, steps 11-14). For each pixel on the Outer Contour, the gradient of the corresponding pixel in the Post image is computed using standard image processing techniques. The MeanGrad is defined as the mean of this set of computed gradient values. One example of a method of using histogram analysis to determine Imax and Imin is illustrated in FIG. 8. A 64×64 pixel subimage containing a lesion was cropped from a breast MRI post-contrast image. The graph in FIG. 8 shows the histogram of pixel intensities within the cropped subimage, after smoothing. Each pixel in the MRI image covers an area approximately equal to 0.4×0.4=0.16 mm². For each intensity level, the approximate area of pixels having that intensity level is computed by multiplying the number of pixels having that intensity level by 0.16 mm². For each intensity level, the approximate area of pixels having that intensity level or greater is computed by summing the areas for all intensity levels greater than or equal to the given intensity level. Intensity level 196, shown by the vertical bar furthest to the right, is the first intensity level such that the area of pixels greater than or equal to that level exceeds an area of 25 mm², corresponding to the parameter Q in the embodiment given above. Intensity level 183, which is used as Imax, shown by the middle vertical bar, is the intensity level at which the histogram reaches its maximum in the right peak of the histogram. The area of pixels having values greater than or equal to Imax is computed as described above. Intensity level 74, which is used as Imin, shown by the left vertical bar, is the highest intensity level such that the area of pixels greater than or equal to that level exceeds the area computed from Imax by a factor of 4, corresponding to the parameter N in the embodiment given above.

$I_{min}$ is set as the lowest intensity level for which the Function of $C_{Imin}$ exceeds the Function of $C_{Imax}$ by some predetermined multiple, i.e., Function $(C_{Imin}) > N*$Function $(C_{Imax})$. (FIG. 3, Steps 1-7.) Alternative criteria for establishing $I_{min}$ can be determined from context, cluster size, cluster numbers, or histogram analysis, within the skill of the ordinary artisan.

Starting with level $I=I_{max}$ and decrementing through $I=I_{min}$, the minimum bounding ROI $B_I$ around $C_I$ is constructed and the Functions representing the characteristics ROIs are computed: $B_{Imax} \subset B_{Imax-1} \subset \ldots$, with Function $(B_{Imax}) \leq$ Function $(B_{Imax-1}) \leq \ldots$. Depending upon the changes in Outer Contours from one intensity level to the next lower intensity level, the minimum bounding ROIs may increase or remain constant. Each time that a decrement in intensity level induces a change in the Function of the minimum bounding ROI, a step counter is incremented. The "step feature" is the final value of the step counter which is output as the total number of steps when B(J)>B (old) where B(old) is the previous minimum bounding ROI. A determination is then made as to whether the lesion is more likely to be benign, cancerous or of an uncertain nature, based on the total number of steps. (FIG. 3, steps 8-12.) It is also contemplated that another number related to the changes in the characteristics of ROI can be used instead of the total number of steps.

FIGS. 4 and 5 show the contours and bounding ROIs, in this case, rectangles for a malignant and benign lesion, respectively. Box 1 shows the cluster at intensity level $I_{max}$. Growth of the cluster (pixels that have been added from the previous intensity level) is shown in black. Bounding boxes that have increased from the previous level are shown with a solid border; bounding boxes that have not increased are shown with a dotted border.

The two lesions have comparable sizes, shapes, and intensity ranges on the MRI images. However, the malignant lesion shows twelve steps (different boxes); the benign lesion shows three such steps.

Note that growth of the cluster occurs at many intensity levels—even for the benign case. In noisy images, growth of the cluster will occur at virtually every intensity level, regardless of the characteristics of the underlying physiological object being studied. The step feature effectively filters out many of the small incidental changes in cluster growth and is relatively insensitive to the placement of the landmark.

DISCLOSURE OF INVENTION

The present invention provides methods for generating image display data that allows images of lesions in a body part to be diagnosed more accurately, and particularly to facilitate accurate diagnosis of malignant lesions.

The methods according to the present invention also make possible the generation of three-dimensional displays from data obtained from a series of mutually parallel planes through the body part.

MODES FOR CARRYING OUT THE INVENTION

Figure 1:
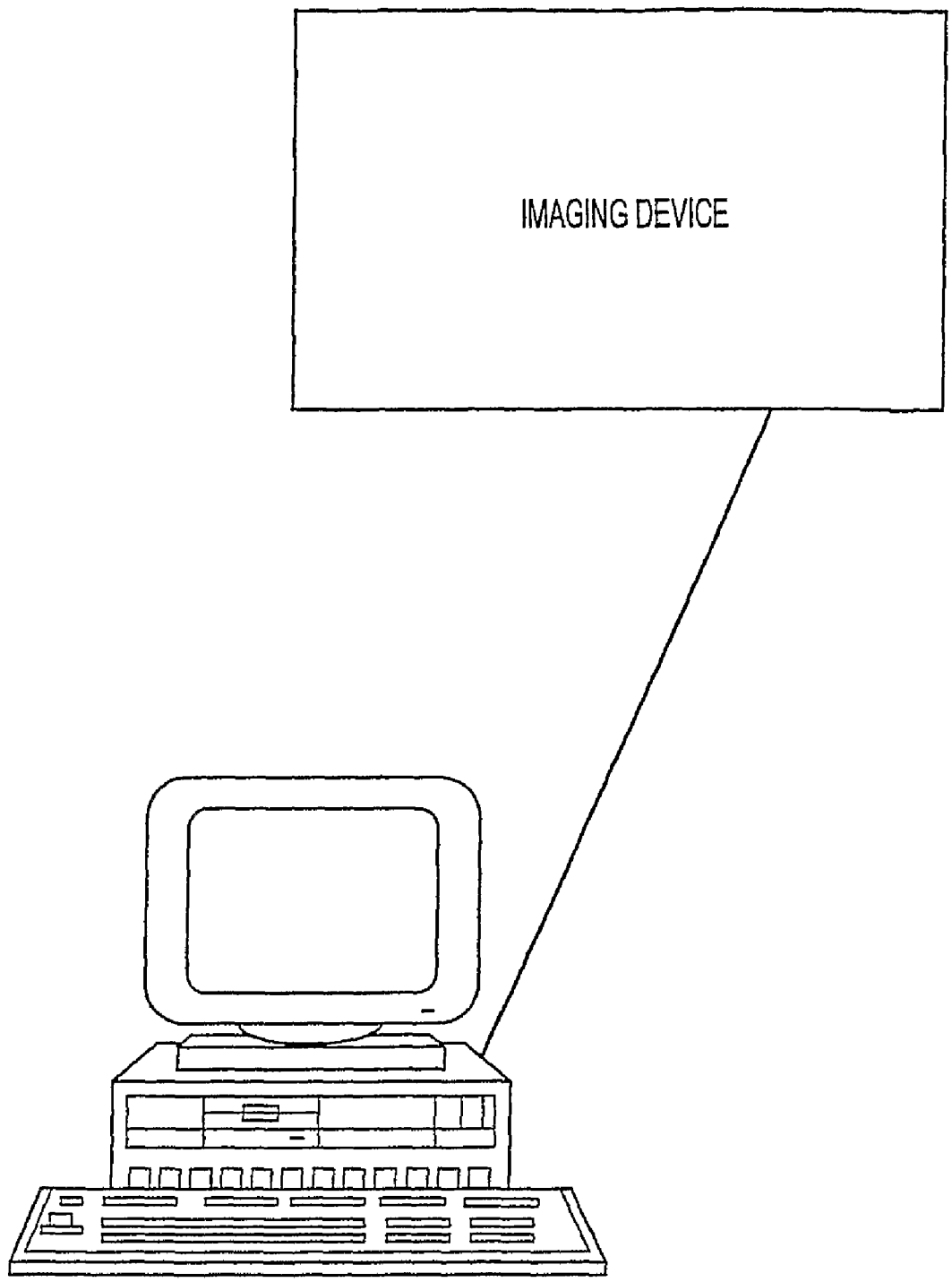
FIG. 1 is a diagram of the imaging device or picture archiving system and computer system according to one embodiment of the invention disclosed in the above-cited applications.
Figure 2:
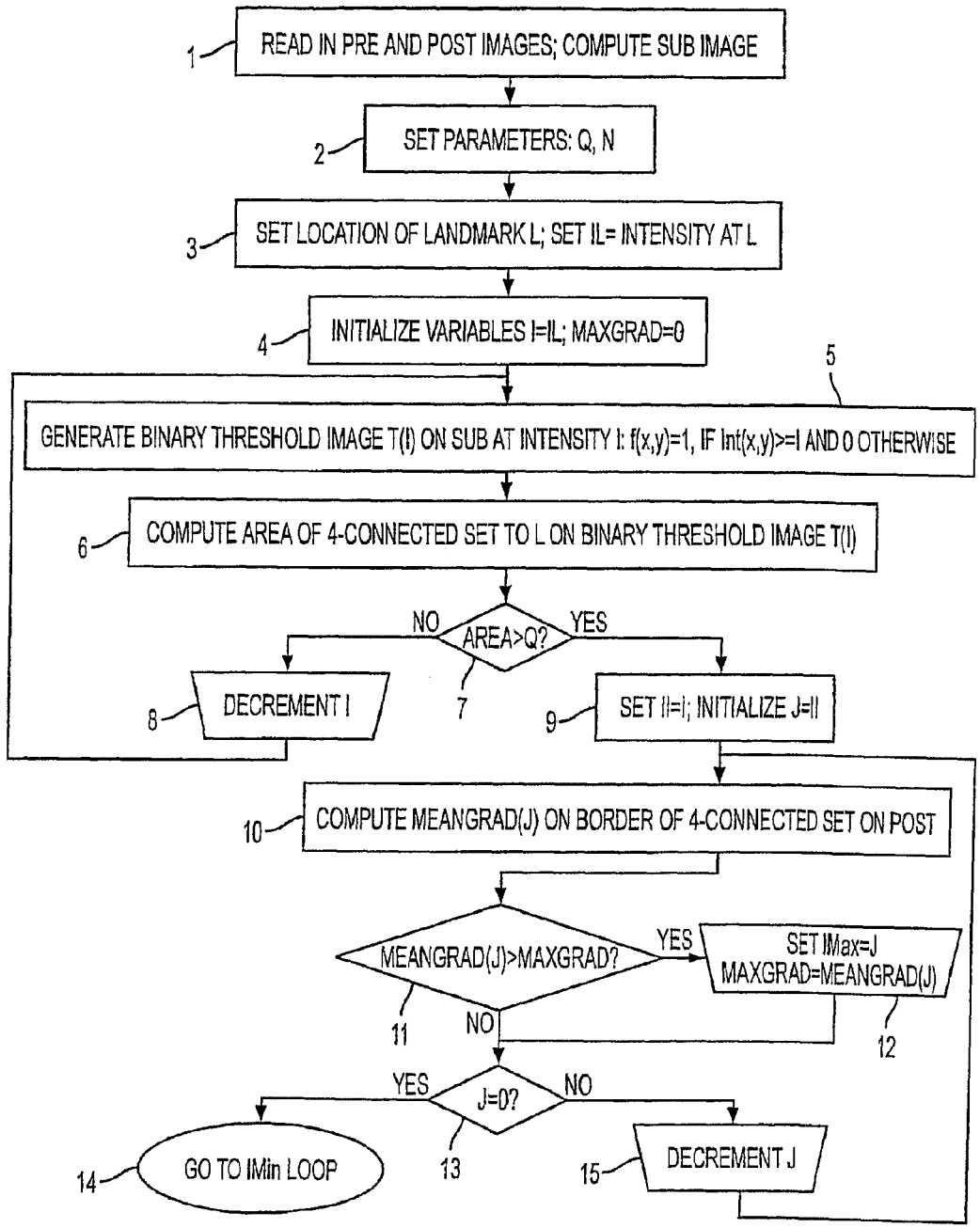
FIG. 2 is a flowchart of the method to initialize and compute $I_{Max}$ in accordance with one embodiment of the invention disclosed in the above-cited applications.
Figure 3:
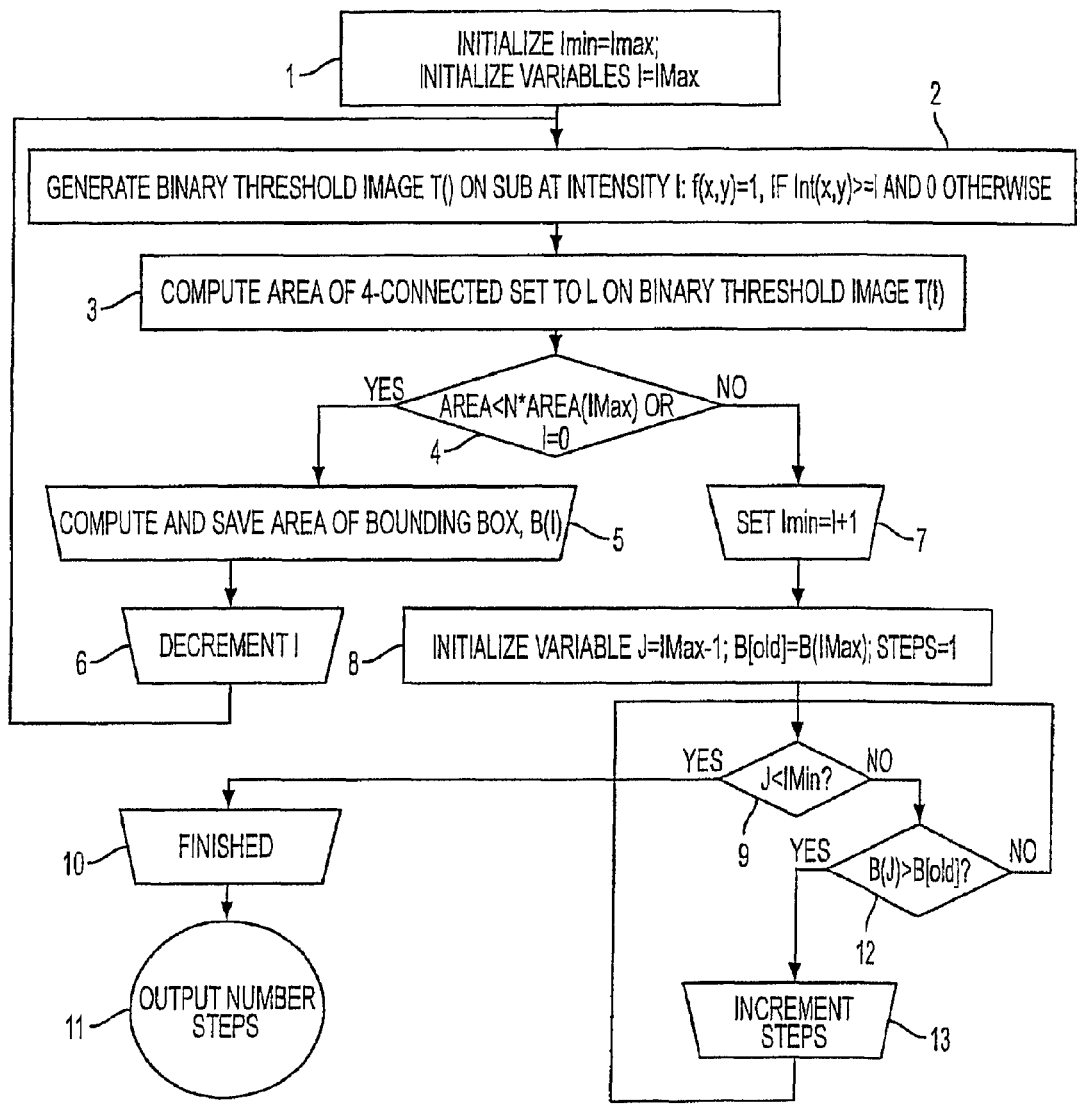
FIG. 3 is a flowchart of the method to compute $I_{Min}$ and number steps, in accordance with one embodiment of the invention disclosed in the above-cited applications.
Figure 4:
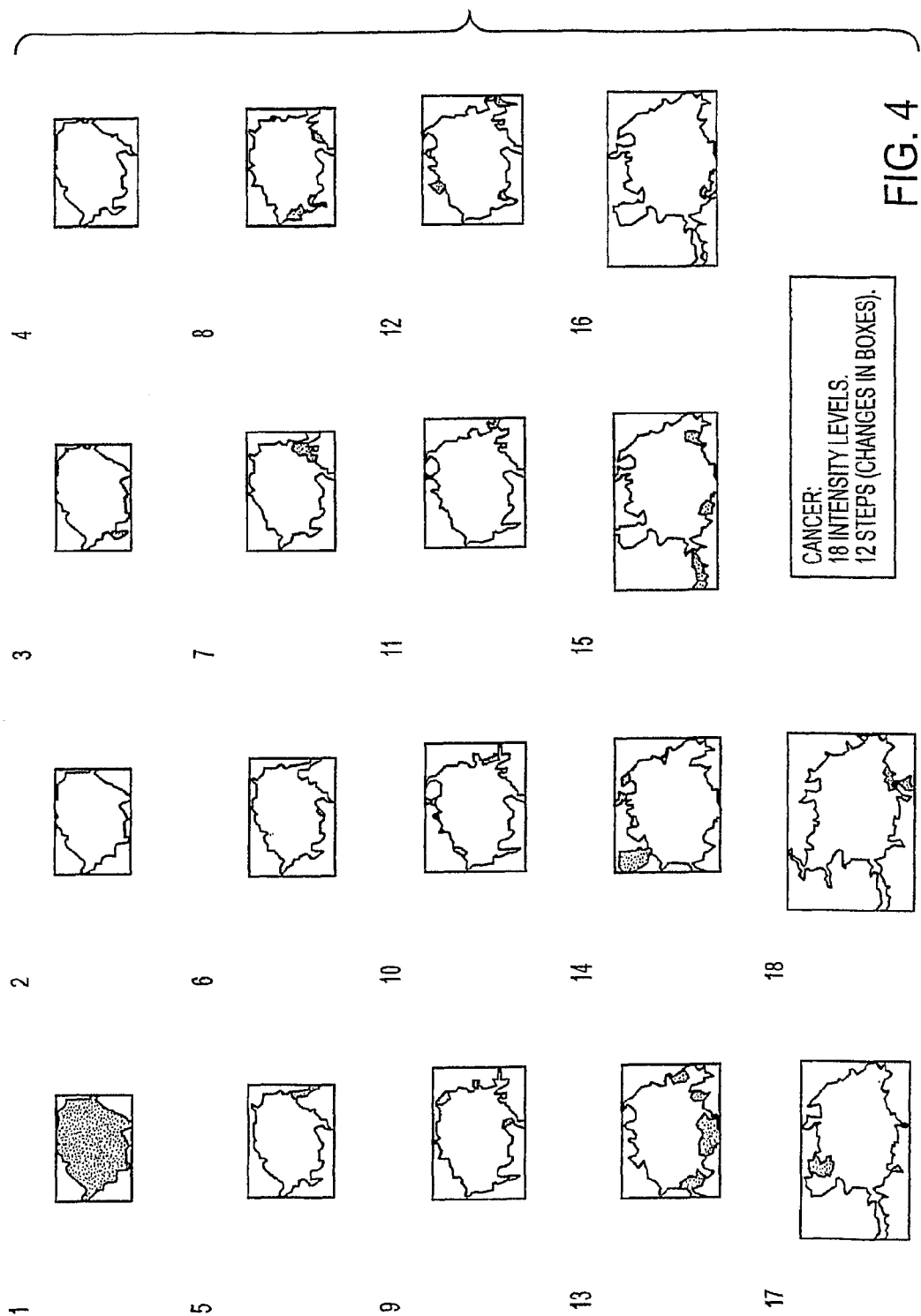
FIG. 4 illustrates the clusters and bounding boxes for a malignant lesion in accordance with one embodiment of the invention disclosed in the above-cited applications.
Figure 5:
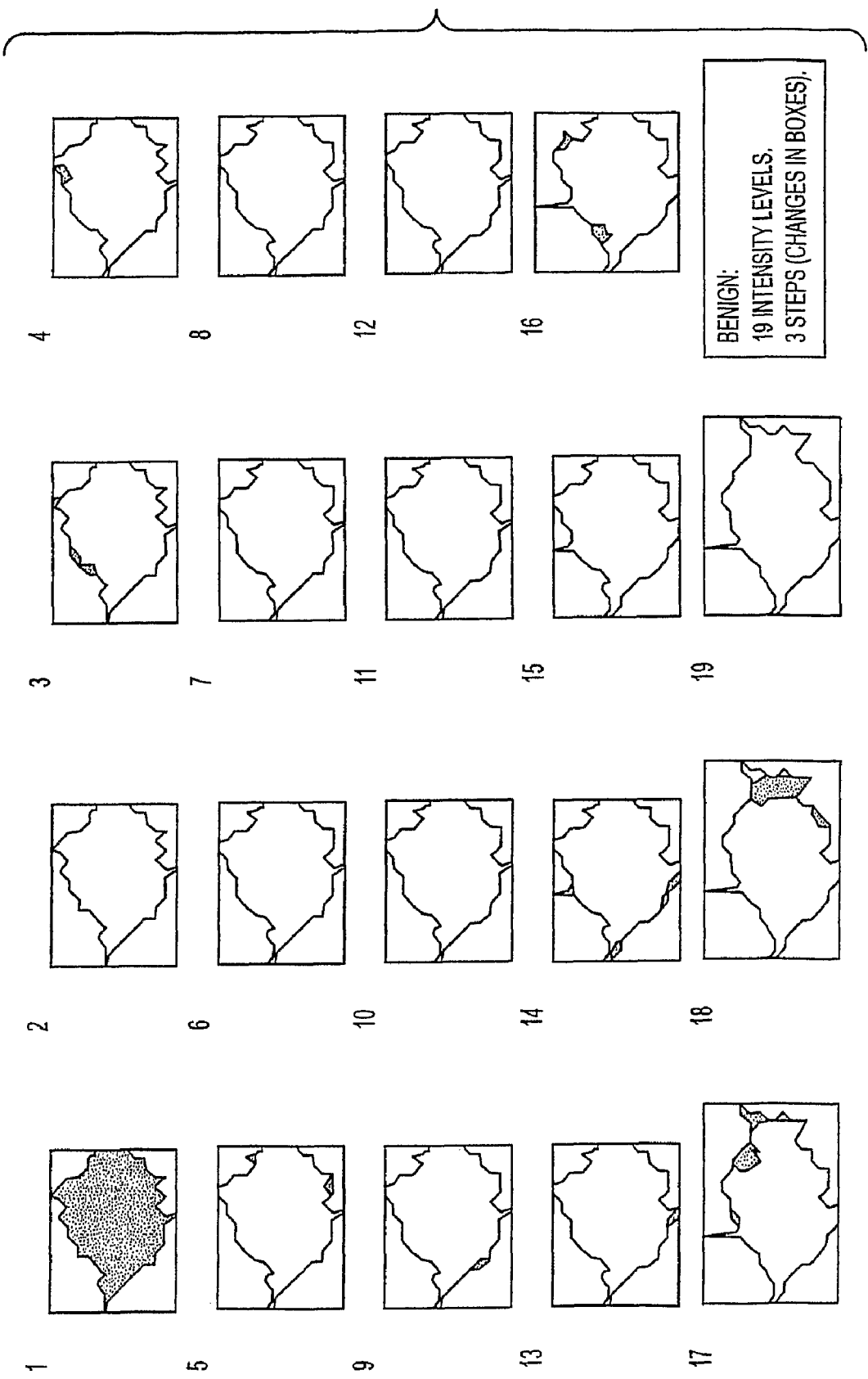
FIG. 5 illustrates the clusters and bounding boxes for a benign lesion in accordance with one embodiment of the invention disclosed in the above-cited applications.
Figure 6:
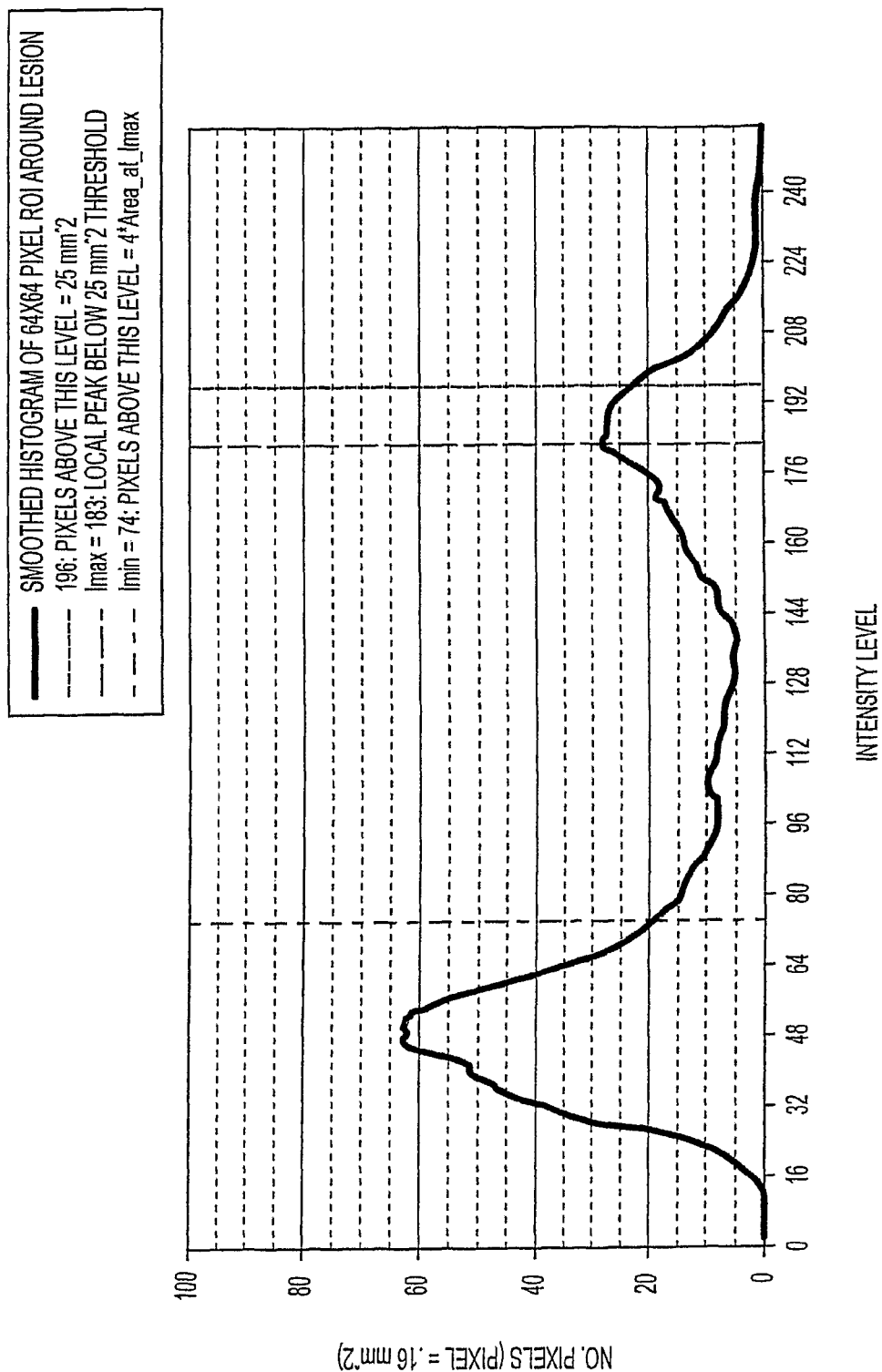
FIG. 6 illustrates one example of a method of using histogram analysis to determine Imax and Imin.

One exemplary procedure according to a first aspect of the invention will now be described.

In a first step, a first data set composed of raw data is obtained, as from signals generated by a system used to aid medical diagnosis, such as MRI systems, for example in the manner described above with reference to the above-cited applications. By this procedure, there is obtained a first data set composed of a matrix of data values, each value representing the intensity of a pixel in an MRI image of a selected planar region of the body part. According to the present invention, such information is obtained for a plurality of mutually parallel planar regions through the body part.

Then, in a second step, the first data sets are converted into second data sets containing, for each pixel in each of the first data sets, data, for example RGB data, representing a particular color and data representing a selected opacity level ($\alpha$). The color is selected on the basis of the intensity of the pixel as represented by the data in the first data set. As a simple example, R is set equal to G which is set equal to B. The opacity level ($\alpha$) is selected to cause the data representing each pixel to contribute a selected proportion to a 3D rendering of all of the image data, as will be explained in greater detail below. This conversion of first data sets into second data sets uses 3D rendering procedures, such as maximum intensity projection (MIP) or surface rendering, such procedures being known to graphic designers. MIP is a specific volume rendering implementation. The basic idea behind MIP is that the value of each pixel in the image is determined by sending a hypothetical ray through the pixel into the volume data according to the current camera or eye position. Then the data encountered along the ray is evaluated using some specified function in order to compute the pixel value. Using MIP, the maximum intensity scalar value along the ray is assigned for the pixel value (as describe by Foley, van Dam, Feiner, Hughes, cited below). A maximum intensity projection (MIP) is a computer visualization method for 3D data that projects in the visualization plane the voxels with maximum intensity that fall in the way of parallel rays traced from the viewpoint to the plane of projection. This technique is computationally fast, but the 2D results do not provide a good sense of depth of the original data. To improve the sense of 3D, animations are often rendered of several MIP frames in which the viewpoint is slightly changed from one to the other, thus creating the illusion of rotation. This helps the viewer's perception to find the relative 3D positions of the object components. This techniques is described and illustrated at http://en.wikipedia.org/wiki/Maximum_intensity_projection.

In a third step, the first data sets obtained in the first step for each planar region are processed to produce respective third data sets that can be used to form contours, where each contour has an associated step number according to the procedures described earlier herein. The third data sets contain pixel data that can then be used, according to those procedures, to form contours, or bounding boxes. The third data set is a map constructed on individual planes from the step functions —i.e., pixels in the first set that correspond to a region with a step value (e.g. a region of enhancement that has a step value=15) have an intensity or colors indicative of that step value.

Then, in a fourth step, the third data sets are processed into fourth data sets by glueing together adjacent planes associated with the third data sets. This involves first thresholding the intensities of the pixels in the third data set at some given value, and then forming n-connected, 3-dimensional clusters, where n is defined to be 6, 18, or 26, as described. For example, two pixels are 6-connected if they are either coplanar and 4-connected, or corresponding pixels with the same (x,y) location in adjacent planar regions. Preferably, each fourth data set is a 6-connected 3-dimensional cluster.

Then, in a fifth step, the fourth data sets are processed into fifth data sets by modifying the pixel intensities within each fourth data set so that all pixels within each fourth data set have the same intensity. By way of example, such a fifth data set may be obtained by setting each pixel within a fourth data set to the mean intensity over the set of pixels within each fourth data set. Preferably, the new intensity value for each pixel (x, y, z) in each fifth data set is set to the value $\mu$, the maximum of smoothed weighted-averages over all planes z within the fourth data set:

$\mu = \max\{M_z\}$, where $M_z = \frac{1}{4}m_{z-1} + \frac{1}{2}m_z + \frac{1}{4}m_{z+1}$, where $m_z = \max\{I(x, y, z)\}$, $m_z$ is the maximum intensity of all pixels within a fourth data set on plane z.

Then, the fifth data sets are converted into sixth data sets containing, for each pixel in each of the fifth data sets, data, for example RGB data, representing a particular color and data representing a selected opacity level ($\alpha$). A particular color is selected for each intensity level or for each range of intensity levels, over a selected intensity range. The opacity level ($\alpha$) is selected to cause the data representing each pixel to contribute a selected proportion to a 3D rendering of all of the image data, such as maximum intensity projection (MIP) which was previously described.

The conversion of each fifth data set into the corresponding sixth data set further includes an additional compositing of the fifth data sets with the second data sets associated with the same planar region in the body part. Compositing involves combining image data to create new image data, e.g., each resulting pixel value is a linear combination of the scalar values of the pixels in the original data. For example, this can involve modifying the data representing each pixel so that each of the RGB and $\alpha$ values is the maximum of the corresponding value of the corresponding pixel of the second data set and the corresponding value of the corresponding pixel of the fifth data set. Alternatively, compositing can involve assigning to each pixel RGB and $\alpha$ values that are each the average of the corresponding values of the corresponding pixels in the second and fifth sets. According to another possibility, which is currently preferred, compositing can involve assigning to each pixel RGB and $\alpha$ values that are the product of each of the respective RGB and $\alpha$ values associated with the pixels in the second set and the fifth sets.

Use of the sixth data sets to produce displays will highlight the likelihood of the existence of a pathological condition.

According to one feature of the invention, the parameters employed in each of the data conversions operations can be independently controlled.

The resulting sixth data sets can then be used to render an apparent 3D display of the body part, either in a plane parallel to the original mutually parallel planes, or in any other plane. The derivation of data for such displays is also based on techniques that are well known in the computer graphics design art.

The purpose of 3D, or volume, rendering is to effectively convey information within volumetric data. Volume rendering is a technique used to represent an entire 3D dataset in a 2D image. [Foley, van Dam, Feiner, Hughes, cited below]

The present invention also provides a further technique for aiding diagnosis of lesions in a body part. This technique basically employs the procedures disclosed in the above-cited applications to produce a display showing two different probabilities of the presence or characteristics of a lesion. According to one possibility, this may be achieved by displaying data processed in the manner described in the above-cited pending applications on the basis of two different maximum mean gradient values. This will result in the display of different visibly distinguishable contours representing different probabilities that the area of interest has a given physiological characteristic, that includes morphology. The different contours can be distinguished by giving the area within each contour a different color, and transparency.

Also incorporated herein by reference are the following texts that describe state of the art techniques that can be used to implement the invention:

Schroeder W, Martin K, Lorensen B. "The Visualization Toolkit: An Objection-Oriented Approach to 3D Graphics". Kitware, Inc., 2004;

Foley, van Dam, Feiner, Hughes. "Computer Graphics: Principles & Practice". Addison-Wesley, 1997.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

Industrial Applicability

The invention is applicable to medical diagnoses from images.

What is claimed is:

1. A method for aiding evaluation of lesions in a body part comprising: in a first step, obtaining a plurality of first data sets each derived from a medical image of a respective one of a plurality of selected planar regions of the body part, each of said first data sets being composed of a matrix of data values, each value representing the intensity of a pixel in the medical image of the respective one of a plurality of mutually parallel planar regions of the body part; in a second step, processing the plurality of first data sets to form a corresponding plurality of second data sets, each of said second data sets containing data representing pixel intensity patterns in the first data sets; in a third step, processing the plurality of first data sets to form a plurality of third data sets, each third data set containing data representing contours or bounding boxes; in a fourth step, processing the plurality of third data sets to form a corresponding plurality of fourth data sets by first thresholding the intensities of the pixels in the third data set at some given value, and then forming n-connected, 3-dimensional clusters; in a fifth step, processing the fourth data sets into fifth data sets by modifying the pixel intensities within each fourth data set so that all pixels within each fourth data set have the same intensity; in a sixth step, converting the fifth data sets into sixth data sets containing, for each pixel in each of the fifth data sets, data, for example RGB data, representing a particular color and data representing a selected opacity level (.alpha.); and using the sixth data sets to produce a display an image of the body part that highlights the likelihood of the existence of a pathological condition.

2. The method of claim 1, wherein said second step is carried out to cause each said second data sets to include data representing, for each pixel of the first data set, a selected opacity level.

3. The method of claim 2, wherein said second step comprises 3D rendering operations.

\* \* \* \* \*